United States Patent [19]

Percival

[11] 4,109,004
[45] Aug. 22, 1978

[54] HALOGENATED ALKYLSULPHONYL-BENZIMIDAZOLES

[75] Inventor: Albert Percival, Hauxton, England

[73] Assignee: Fisons Limited, England

[21] Appl. No.: 826,817

[22] Filed: Aug. 22, 1977

[30] Foreign Application Priority Data

Aug. 25, 1976 [GB] United Kingdom ............... 35306/76

[51] Int. Cl.$^2$ .................. C07D 235/22; A61K 31/415
[52] U.S. Cl. .................................. 424/273 R; 548/329
[58] Field of Search ...................... 548/329; 424/273 R

[56] References Cited

U.S. PATENT DOCUMENTS

| 2,603,649 | 7/1952 | Clapp et al. | 548/329 |
| 2,980,679 | 4/1961 | Pala | 548/329 |
| 3,430,259 | 2/1969 | Newbold et al. | 548/329 |
| 3,920,681 | 11/1975 | Buchel et al. | 548/329 |

FOREIGN PATENT DOCUMENTS

| 1,439,128 | 4/1966 | France | 548/329 |
| 1,439,129 | 4/1966 | France | 548/329 |

OTHER PUBLICATIONS

Charlson, Carbohyd. Res., 1973, vol. 29, pp. 89–98.
Haugwitz et al., Chem. Abst., 1972, vol. 77, No. 164695w.
Lutz et al., Chem. Abst., 1970, vol. 72, No. 31798g.

Primary Examiner—Natalie Trousof
Attorney, Agent, or Firm—Wenderoth, Lind & Ponack

[57] ABSTRACT

There are provided substituted benzimidazoles of the formula:

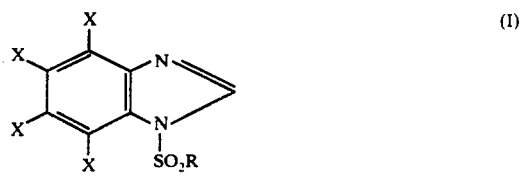

(wherein at least two of the radicals X are halogen and the remainder are hydrogen, and R represents an alkyl radical of 1 to 6 carbon atoms), processes for preparing them, and compositions containing them.

The compounds possess anti-protozoal activity.

11 Claims, No Drawings

HALOGENATED ALKYLSULPHONYL-BENZIMIDAZOLES

This invention concerns certain substituted benzimidazoles, processes for their preparation, and compositions containing them.

In one aspect, this invention provides the substituted benzimidazoles of the formula:

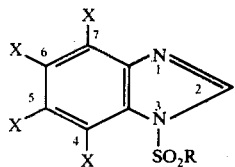

(wherein at least two of the radicals X are halogen and the remainder are hydrogen, and R represents an alkyl radical of 1 to 6 carbon atoms).

The halogen which the radicals X may represent may be bromine or iodine, but is preferably chlorine.

Preferably, the two or more radicals X which represent halogen all represent the same halogen.

Desirably two only of the radicals X represent halogen, particularly those at the 5- and 6- positions.

R preferably represents an alkyl radical of 1 to 4 carbon atoms, for example ethyl, n-propyl, isopropyl or n-butyl, and especially methyl.

A particularly preferred compound of formula I is 5,6-dichloro-1-(methylsulphonyl)benzimidazole.

The compounds of formula I may be prepared by a process in which a substituted benzimidazole of the formula:

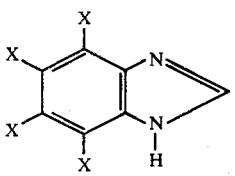

(wherein the radicals X are as defined hereinbefore) is reacted with an alkanesulphonyl halide of the formula:

 YSO$_2$R (III)

(wherein R is as defined hereinbefore and Y represents halogen) in the presence of an acid acceptor.

The halogen which Y represents is preferably chlorine.

The acid acceptor is preferably an organic base, for example a tertiary base, e.g. triethylamine.

The compounds of formula I possess activity against protozoan parasites, for example of the genus Eimeria, such as *E tenella, E necatrix, E acervulina, E maxiria, E hagani*, and *E brunetti*. They are therefore of use in combating protozoan infections in animals, and especially coccidiosis in poultry.

In another aspect, therefore, this invention provides a method of combating protozoa in an animal, which method comprises administering to said animal one or more compounds of formula I in an amount sufficient to exert its anti-protozoal effect.

The compounds of formula I are normally employed in the method of the present invention in the form of compositions comprising one or more compounds of formula I in association with a suitable pharmaceutically-acceptable carrier and/or surface-active agent, or as additives to the drinking water or food of the animal.

In another aspect, therefore, this invention provides antiprotozoal compositions comprising one or more compounds of formula I in association with a suitable pharmaceutically-acceptable carrier and/or surface active agent.

The compositions may be administered orally, by injection, or dermally, and the carrier and/or surface active agent must of course be chosen according to the desired method of administration. A desired dose is from 0.1 to 10 mg/kg body weight, repeated as necessary.

For oral administration, the compounds are desirably incorporated into the diet of the animal in an amount of from 0.001 to 0.1%; especially from 0.002 to 0.015% by weight.

Formulations for adding to drinking water should include surface active agents to ensure satisfactory solution or dispersion.

Formulations for adding to food may consist of the compound alone or admixed with physiologically acceptable carriers such as talc, chalk, gypsum or earths, with or without surface active agents.

The compounds may be formulated by impregnating or coating a granule, for example a gypsum granule, with them.

A composition may contain as carrier a foodstuff for the animal.

For administration by injection, the compositions are preferably sterile.

For dermal application, the compounds may be administered in compositions as described in our British Pat. No. 1,464,552.

The composition may be in unit dosage form, e.g. a tablet or capsule, containing 150 – 1,500 mg of the compound.

The compounds of formula I are envisaged for use especially in poultry, e.g. chickens, ducks, geese, turkeys, pheasants, partridges, grouse and quail.

The compounds of formula I are water insoluble, and may be formulated into an appropriate composition by any of the methods commonly employed for insoluble compounds.

For example, the compounds of formula I may be dissolved in a water immiscible solvent, for example a high boiling hydrocarbon, as carrier.

Alternatively, for oral administration, the carrier may be a solid, e.g. talc, chalk, gypsum or earths.

The surface active agents used may comprise anionic surface active agents, for example mono- or di-esters of phosphoric acid with fatty alcohol ethoxyplates or salts of such esters, fatty alcohol sulphates such as sodium dodecyl sulphate, ethoxylated fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialyl sulphosuccinates e.g. the sodium sulphonate of dioctyl succinate.

The surface active agents may also comprise nonionic agents, for example condensation products of fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quarternary ammonium compounds such as cetyl trimethylammonium bromide, or ethoxylated tertiary fatty amides.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, sodium oleoyl N-methyltauride, dialkyl sulphosuccinates, alkyl phenol ethoxylates, and fatty alkyl ethoxylates.

The term 'surface active agent' is used in the broad sense to cover materials variously called wetting agents, emulsifying agents and dispersing agents. Such agents are well known.

The compositions may contain other anti-protozoal compounds or other compounds which stimulate the growth or health of the animal.

The compounds may be used to inhibit infection or to treat an infection already present.

The invention will now be described, though only by way of illustration, in the following Examples, wherein all parts and percentages are by weight.

EXAMPLE 1

Synthesis of 5,6-dichloro-1-(methylsulphonyl)benzimidazole

A solution of methanesulphonyl chloride (60 parts) in acetone (800 parts) was added dropwise to a suspension of 5,6-dichloro-benzimidazole (94 parts) in acetone (240 parts) containing triethylamine (50 parts). A precipitate of triethylamine hydrochloride was observed and the temperature rose to 40° C. The mixture was heated under reflux for 10 minutes and then stirred at room temperature for 20 hours. On pouring into cold water (4000 parts) a solid product precipitated out, which was filtered off, washed with water, dried and recrystallised from acetone (charcoal) to give 5,6-dichloro-1-(methylsulphonyl)-benzimidazole (61 parts) as pale yellow needles, melting point 191°–193° C.

Analysis — Found: C, 36.36; H, 2.58; N, 10.28%. $C_8H_6Cl_2N_2O_2S$ requires: C, 36.24; H, 2.28; N, 10.57%

EXAMPLE 2

Efficacy against *Eimeria tenella*

Four groups of chickens 7 days old were infected orally with 40,000 sporulated oocysts *E tenella*. Three of the groups were administered 5,6-dichloro-1-(methylsulphonyl)benzimidazole in the diet, at the concentrations shown in the table below, commencing 2 days before infection. The fourth group were left as un-medicated controls. The efficacy of the treatment was assessed by comparing the mortality of the medicated groups with that of the un-medicated infected controls and also by comparing the weight gain of medicated groups with that of an un-medicated un-infected group. The test was continued for 7 days after infection. The results obtained are in the table below.

| Dietary Concentration | % Reduction* Mortality | % Weight** Gain |
|---|---|---|
| 0.0125% | 100 | 100 |
| 0.006% | 100 | 86.7 |
| 0.003% | 60 | — |

*Compared with infected controls
**Compared with non-infected controls

A dietary concentration of 0.0125% gave 100% reduction of mortality due to coccidiosis and weight gain was the same as that of non-infected chicks. A dose response was demonstrated.

EXAMPLE 3

Efficacy against *Eimeria acervulina*

A test similar to that described above was carried out with *E acervulina*. Assessment in this experiment was by comparing the oocyst output of medicated groups with non-medicated controls. The results are tabulted below.

| Dietary Concentration | % Reduction oocyst output |
|---|---|
| 0.006% | 77.5 |

Medication of chicks infected with E acervulina with 5,6-dichloro-1-(methylsulphonyl)benzimidazole at a dietary concentration of 0.006% reduced the number of oocysts produced by the birds by 77.5% compared with non-medicated infected birds.

I claim:

1. A substituted benzimidazole of the formula:

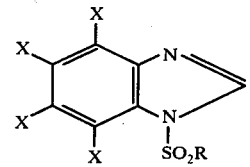

wherein at least two of the radicals X are halogen and the remainder are hydrogen, and R represents an alkyl radical of 1 to 6 carbon atoms.

2. A compound according to claim 1 wherein the halogen which the radicals X may represent is chlorine.

3. A compound according to claim 1 wherein two only of the radicals X represent halogen.

4. A compound according to claim 1, wherein R represents methyl.

5. 5,6-Dichloro-1-(methylsulphonyl)benzimidazole.

6. An anti-protozoal composition comprising an anti-protozoally effective amount of a compound according to claim 1 together with a pharmaceutically-acceptable carrier or surface active agent or both.

7. A composition according to claim 6 wherein the carrier is an animal foodstuff.

8. A method of combating protozoa in an animal, which method comprises administering to said animal an anti-protozoally effective amount of a compound claimed in claim 1.

9. A method according to claim 8 wherein the compound is administered to poultry.

10. A method of combating protozoa in an animal which method comprises administering to said animal an anti-protozoally effective amount of a composition according to claim 7.

11. A method according to claim 10 wherein the composition is administered to poultry.

* * * * *